US012643845B2

(12) United States Patent
Bartman et al.

(10) Patent No.: US 12,643,845 B2
(45) Date of Patent: Jun. 2, 2026

(54) COLORLESS MONOCHLOROACETIC ACID AND THE METHOD OF PREPARATION THEREOF

(71) Applicant: PCC MCAA SP. Z O.O., Brzeg (PL)

(72) Inventors: Marcin Bartman, Wroclaw (PL); Paulina Szczepaniak, Brzeg (PL); Dominika Czachór, Wroclaw (PL); Katarzyna Komor, Wroclaw (PL)

(73) Assignee: PCC MCAA SP. Z O.O., Brzeg Dolny (PL)

( * ) Notice: Subject to any disclaimer, the term of this patent is extended or adjusted under 35 U.S.C. 154(b) by 544 days.

(21) Appl. No.: 18/003,460

(22) PCT Filed: Jun. 28, 2021

(86) PCT No.: PCT/PL2021/050046
§ 371 (c)(1),
(2) Date: Dec. 27, 2022

(87) PCT Pub. No.: WO2022/005315
PCT Pub. Date: Jan. 6, 2022

(65) Prior Publication Data
US 2023/0312450 A1     Oct. 5, 2023

(30) Foreign Application Priority Data
Jun. 28, 2020    (PL) ......................................... 434487

(51) Int. Cl.
*C07C 51/50*          (2006.01)

(52) U.S. Cl.
CPC ..................................... *C07C 51/50* (2013.01)

(58) Field of Classification Search
CPC .............................. C07C 51/50; C07C 51/487
See application file for complete search history.

(56) References Cited

U.S. PATENT DOCUMENTS 5,756,840 A * 5/1998 Ebmeyer ............... C07C 51/487
562/604

FOREIGN PATENT DOCUMENTS

EP           1451136 A2     9/2004

OTHER PUBLICATIONS

International Search Report and Written Opinion dated Oct. 11, 2021, issued in Application No. PCT/PL2021/050046 (11 pages).

* cited by examiner

*Primary Examiner* — Deborah D Carr
(74) *Attorney, Agent, or Firm* — Fox Rothschild LLP

(57) ABSTRACT

An improved method of producing monochloroacetic acid (MCAA) is disclosed, which affords a colorless monochloroacetic acid product in any form that can be obtained by this method.

16 Claims, 4 Drawing Sheets

1

COLORLESS MONOCHLOROACETIC ACID AND THE METHOD OF PREPARATION THEREOF

CROSS-REFERENCE TO RELATED APPLICATIONS

This application is the U.S. national phase application under 35 U.S.C. § 371 of International Patent Application No. PCT/PL2021/050046 filed Jun. 28, 2021, which claims the benefit of priority to Polish Patent Application No. P.434487 filed Jun. 28, 2020, the disclosures of which are hereby incorporated by reference herein in their entireties.

The present invention relates to an improved method for producing monochloroacetic acid (MCAA), which affords a colorless product in any form. The method according to the invention is for the industrial production of substantially colorless MCAA. The invention also relates to stable, substantially colorless MCAA in any form.

Monochloroacetic acid derivatives are currently used in many industries, including in the food, dye, cosmetic, mining and plant protection industries. Their production uses MCAA in various product forms, including solid form, the so-called MCAA flakes (solid granules), undiluted liquid form (molten 100% MCAA stored at a temperature of at least 70° C.), liquid form diluted with water (60-90% MCAA aqueous solution).

It is known that during the industrial production of monochloroacetic acid, especially at the stage of chlorination, hydrogenation or distillation, various types of organic impurities can be formed, which circulate in all process streams in greater or lesser concentration. On an industrial scale, this is a significant problem because it contributes to a reduction in the thermal stability of crude monochloroacetic acid obtained in the known production processes, in particular when the fresh catalyst for the hydrogenation process is put into use. In the first cycle of use, the fresh hydrogenation catalyst shows a very high activity, as a consequence of which the production of trace amounts of organic by-products is observed during the process, which potentially can gradually negatively affect the thermal stability of the final products. As a result, when MCAA is stored in the form of end products, such as MCAA flakes, molten MCAA, or aqueous MCAA solution, there is a risk that such end products during storage may gradually turn light yellow or light brown or light gray, etc., especially at elevated temperatures. The visual color change of the samples does not affect the processing of monochloroacetic acid in further chemical and industrial processes.

After replacing and using a fresh catalyst of the hydrogenation process, when it showed very high activity, samples of molten 100% MCAA and aqueous solution of MCAA were taken to verify the thermal stability of the final products over time and at elevated storage temperature.

The results of the MCAA color stability tests are shown in Table 1. The tests were performed in two independent replications (1) and (2), each time with two different samples of molten 100% MCAA or 80% MCAA water solution, which were stored for 7 days under accelerated aging conditions. i.e. 70° C. or 40° C., respectively. The color of the product was measured at the start of the test (measurement at time 0) and on the following days of the test.

2

TABLE 1

Crude MCAA color change (100% or 80%) when stored at elevated temperature (70° C. or 40° C.) for 7 days. The color level was determined on Hazen scale. The color of the product was measured at the beginning of the test (measurement 0) and after the selected test days (i.e., days 1 and 7).

|  | Color in Hazen units - incubation at 70° C., day of measurement | | |
| --- | --- | --- | --- |
| 100% MCAA | 0 | 1 | 7 |
| 100% MCAA (1) | <60 | <60 | >60 |
| 100% MCAA (2) | <60 | >60 | >60 |
|  | Color in Hazen units - incubation at 40° C. | | |
| 80% MCAA | 0 | 1 | 7 |
| 80% MCAA (1) | <20 | <20 | >20 |
| 80% MCAA (2) | <20 | >20 | >20 |

The risk of color change during storage occurs, in particular, in the period after replacement and/or when the fresh catalyst for the hydrogenation process is put into use, and may have a negative effect on the long-term storage of the product, especially at elevated temperatures.

Therefore, in the industrial-scale production of MCAA, there is a need to solve this problem and ensure the thermal stability of the end products.

U.S. Pat. No. 5,756,840 relates to a method for producing monochloroacetic acid in which a melt crystallization is performed after the hydrogenation step.

EP 1451136B1 relates to a method for producing monochloroacetic acid in which the aldehydes present in the chlorination and hydrogenation process stream are removed by peroxidation using peroxycarboxylic acid, where this acid is dosed into the acetic acid recycle stream to the chlorination unit.

JP 1992338357A relates to a method for purifying acetic acid which comprises addition of hydrogen peroxide thereto and then distilling it to remove impurities, especially aldehydes.

The prior art inventions do not, however, solve the problem of the risk of color change during the storage of pure, raw MCAA, particularly in the period after replacement and/or when the fresh catalyst for the hydrogenation process is put into use.

Moreover, the inventors have found that the hydrogen peroxide does not remain inert towards both monochloroacetic acid and dichloroacetic acid, causing an increase in dichloroacetic acid and trichloroacetic acid in the end product, which is an undesirable effect.

The prior art describes the use of peroxycarboxylic acids in the chlorination and hydrogenation steps in the production of MCAA in order to eliminate aldehydes from process circulation streams by peroxidation, however, this carries significant risks of a dangerous disruption of the synthesis process. In particular, there is a risk that unreacted peroxycarboxylic acid will get to the hydrogenation catalyst, initiating an uncontrolled increase in temperature in the catalytic bed in the reactor and a significant increase in side reactions resulting in a loss of selectivity of the hydrogenation reaction. At the same time, it is known that in particular in the initial period after the replacement and/or when the fresh catalyst of the hydrogenation process is put into use, it shows high activity and relatively low selectivity of the hydrogenation reaction manifested by increased production of aldehydes and their condensates through the catalytic bed, and thus their greater amounts are present in process streams, which also requires the use of significant amounts of peracetic acid, which in turn affects the production costs of MCAA. The use of aqueous solutions of peroxycarboxylic acids in the chlorination and hydrogenation step during production is also disadvantageous, because the additional amount of water introduced into the system at these production steps causes losses in the form of deactivation of the chlorination process catalyst and contributes to the formation of glycolic acid esters resulting from the hydrolysis of monochloroacetic acid.

OBJECT OF THE INVENTION

The object of the invention is to provide an industrial method for obtaining substantially colorless, time-stable 100% MCAA products in solid form, preferably white flakes or granules, or in liquid form, undiluted, preferably with a color not exceeding 100 units on Hazen scale, or in substantially colorless, diluted with water, liquid form, at a MCAA concentration of 60-90%, preferably with a color not exceeding 60 units on Hazen scale, and ensuring high thermal stability of the end products, in particular, in the initial period of production after replacement and/or when the fresh catalyst of the hydrogenation process is put into use.

A particular object of the invention is to provide a method for preparing stable colorless MCAA form, in particular, in the initial period of production after replacement and/or when the fresh catalyst of the hydrogenation process is put into use, which method would not interfere with the earlier steps of the MCAA production technology and could be applied directly to the raw MCAA obtained after final distillation. When producing MCAA in solid or liquid form, diluted with water, it is desirable that the decolorization process is performed immediately prior to final packaging and/or prior to dilution with water of monochloroacetic acid to obtain the final form of a commercial product (i.e. MCAA flakes or 60-90% MCAA aqueous solution).

The present invention describes a solution to the above-mentioned problems and provides colorless, time-stable MCAA end products in liquid form as well as white MCAA end products in solid form, particularly when the production of by-products by the catalytic bed negatively affects the thermal stability of the products, in the initial period after the replacement and/or when the fresh catalyst of the hydrogenation process is put into use.

The Essence of the Invention

Unexpectedly, the object defined above was achieved with the method of obtaining MCAA according to the invention.

The subject of the invention is a method for producing colorless monochloroacetic acid, in particular applicable when the production of by-products by the catalytic bed has a negative effect on the thermal stability of the products, characterized in that it comprises a step of peroxidation of crude monochloroacetic acid, in which the peroxycarboxylic acid, preferably peracetic acid, is added to the crude monochloroacetic acid in liquid form, in an amount of at least 50 ppm based on the weight of the monochloroacetic acid, and the peroxidation reaction is carried out at a temperature of 20° C. to 100° C. to obtain a colorless product with a color level below 100 units on Hazen scale. Then, if necessary, the product is cooled to room temperature, optionally water is added, and packaged, wherein pure monochloroacetic acid in molten form or water-diluted monochloroacetic acid with a concentration above 60 wt %, preferably monochloroacetic acid diluted with water with a concentration of 60 wt % to 90 wt % is used as the raw monochloroacetic acid.

Preferably, the peroxycarboxylic acid is peracetic acid.

Preferably, the peroxycarboxylic acid is used in the form of an aqueous solution with a concentration of 10% to 25% of the peroxycarboxylic acid.

Preferably, the peroxycarboxylic acid is used in an amount of 50-1000 ppm based on the weight of pure, preferably molten, monochloroacetic acid.

Preferably, the peroxycarboxylic acid is used in an amount of 50-1000 ppm based on the weight of the water-diluted monochloroacetic acid with a concentration of 60 wt % to 90 wt %.

Preferably, the peroxidation of the undiluted monochloroacetic acid is carried out at a temperature of 70-100° C.

Preferably, the peroxidation of the water-diluted monochloroacetic acid is carried out at a temperature of 20-80° C.

Another object of the invention is colorless monochloroacetic acid, characterized in that it maintains a color level of less than 60 units on Hazen scale for at least 7 days when stored at a temperature of not more than 70° C.

The color measurement should be performed according to the commonly known procedures for determining the intensity of the yellow color of a solution based on the scale developed by Allen Hazen (Allen Hazen. The Measurement of the Colors of Natural Waters. Journal of the American Chemical Society. 18 (3), p. 264-275, March 1896) based on standard Pt/Co aqueous solutions of various concentrations and known as Hazen scale (also referred to as: platinum-cobalt scale, Pt/Co scale or Apha-Hazen scale). According to the invention, the measurement of the color intensity on Hazen scale may be performed by any known procedure, in particular one of the procedures detailed in the relevant industry standards (e.g. PN-81/C-04534, ASTM D 1209 (2005), BS 5339 (1976), ISO 2211:1973, DIN EN ISO 6271-1:2005) including measuring the color intensity of a liquid with a spectrophotometer.

Preferably, the monochloroacetic acid according to the invention is characterized in that it has a form selected from:

100% monochloroacetic acid in solid form, preferably granules or flakes, or in liquid form, in particular 100% monochloroacetic acid in molten form, water-diluted monochloroacetic acid with a concentration of 60 wt % to 90 wt % in liquid form.

When measuring the color of a solid MCAA, e.g. in the form of a flakes, it must first be liquefied for measurement by diluting with distilled water to an 80% MCAA solution.

Preferably, the monochloroacetic acid according to the invention is characterized in that it has been obtained by the method according to the invention as defined above.

DETAILED DESCRIPTION OF THE INVENTION

Figure 1:
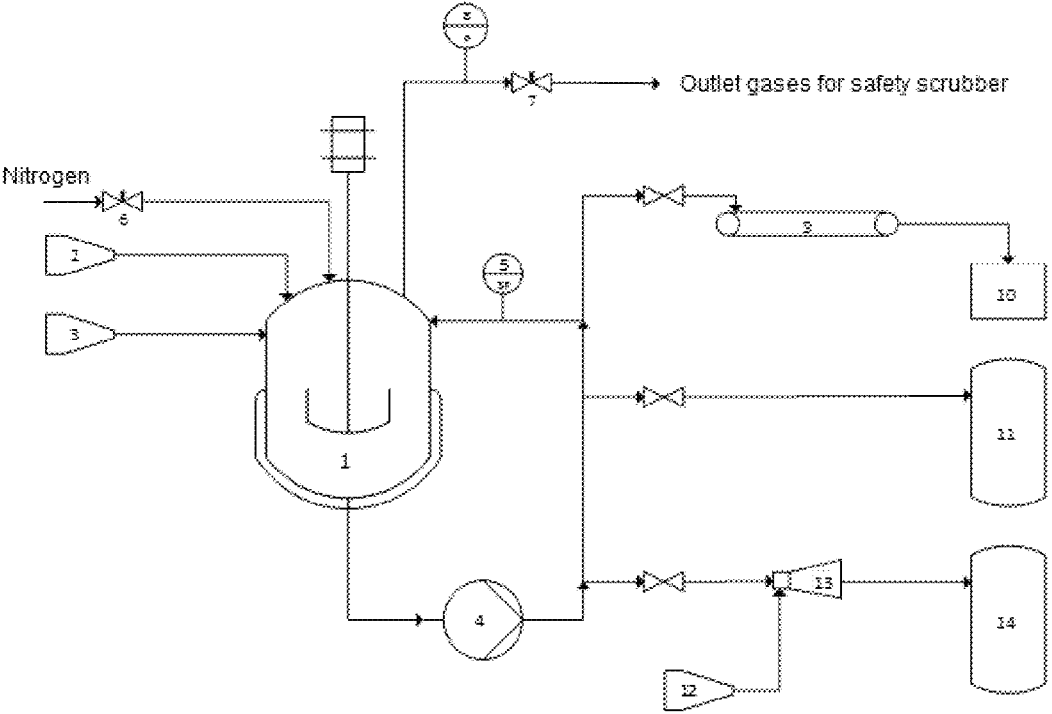
FIG. 1 shows a schematic diagram of the test stand for testing the thermal stabilization of monochloroacetic acid.
Figure 2:
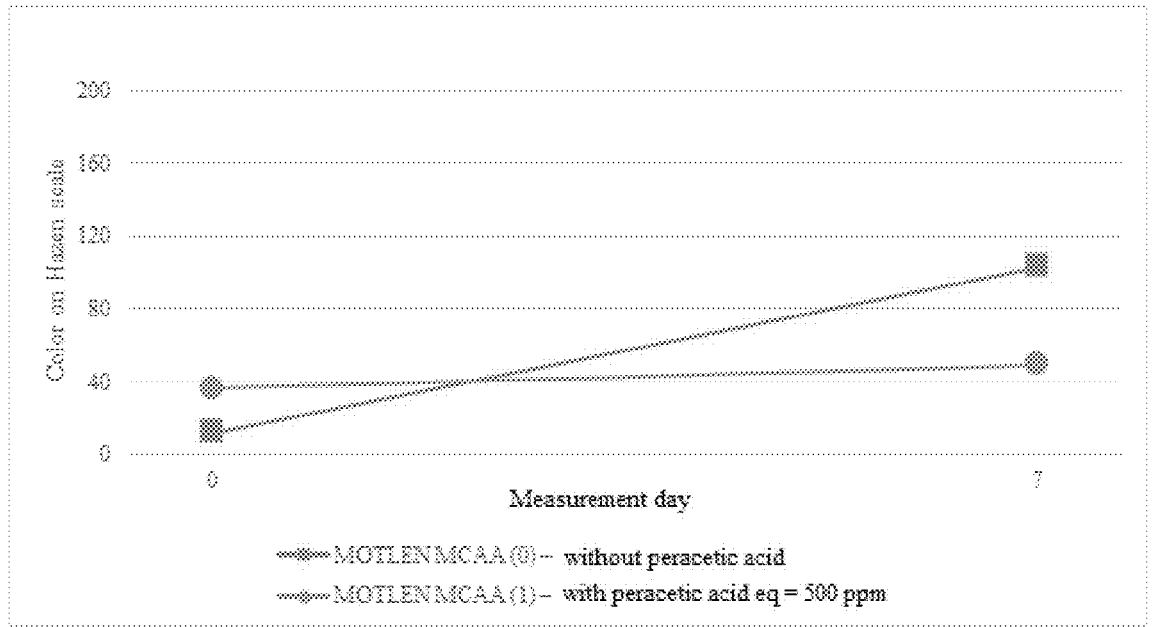
FIG. 2 shows a color measurement (Hazen scale) of MCAA according to Example 1.
Figure 3:
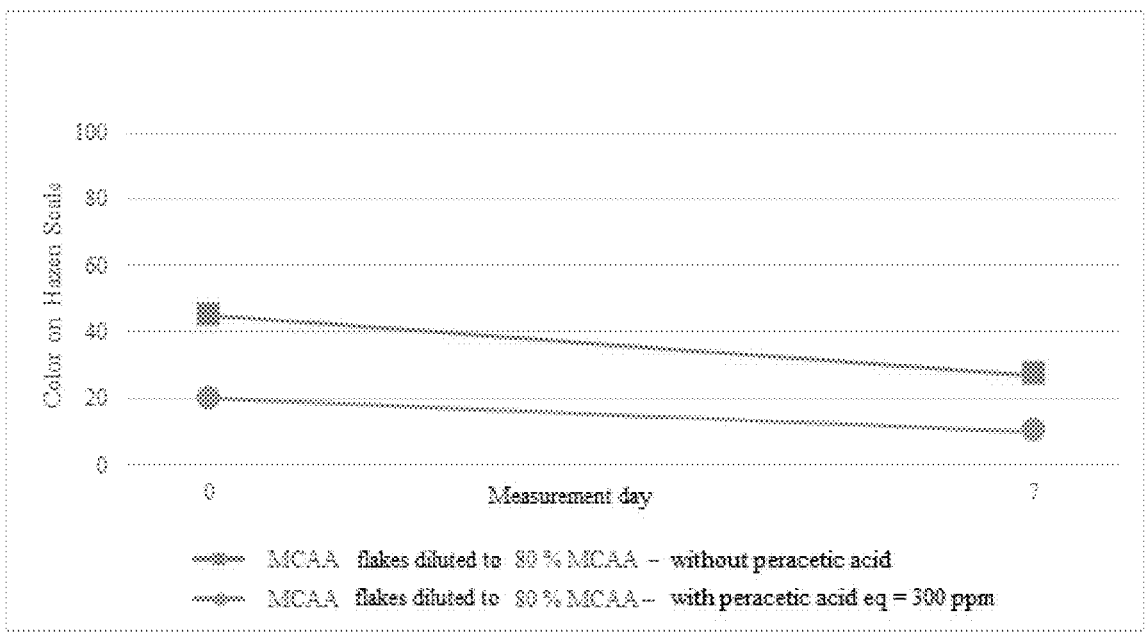
FIG. 3 shows a color measurement (Hazen scale) of MCAA according to Example 2.
Figure 4:
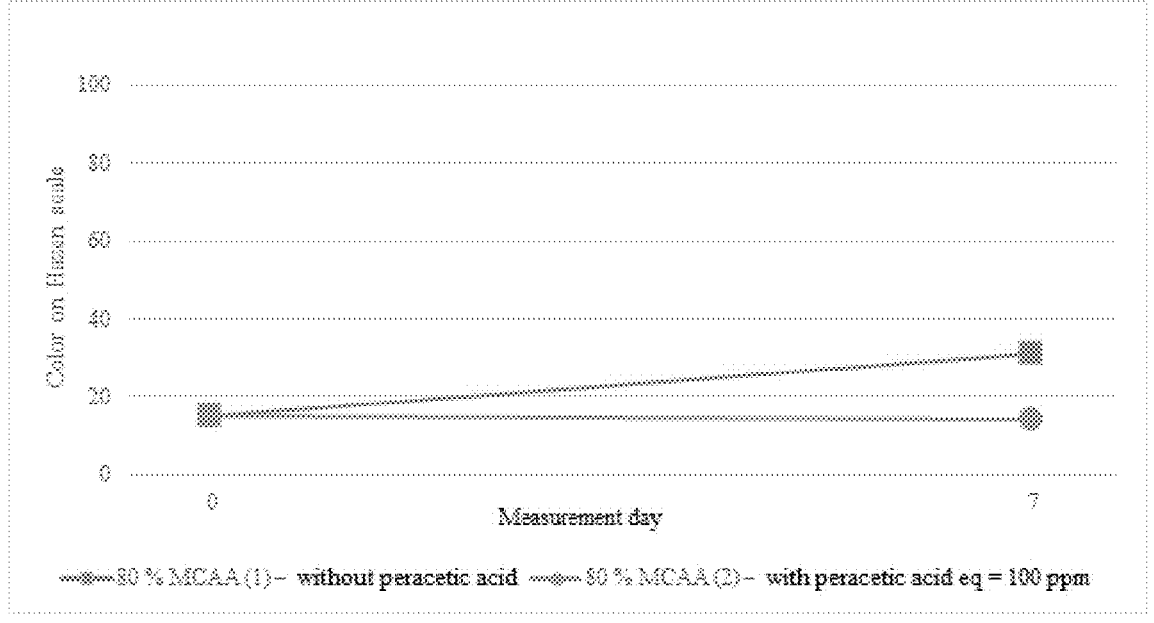
FIG. 4 shows a color measurement (Hazen scale) of MCAA according to Example 3.

The invention relates to a method for preparing a permanently colorless monochloroacetic acid, in any product form, comprising a step after distillation and/or before packaging and/or before diluting the monochloroacetic acid with water by thermally stabilizing the trace impurities by peroxidating them with peroxycarboxylic acid in order to ensure the inertness of organic impurities sensitive to high temperature, which are responsible for accelerating the aging of the final products, i.e. monochloroacetic acid in the molten form, monochloroacetic acid in the solid form, monochloroacetic acid diluted with water at a concentration of 60-90%, which is manifested by an increase in the color of the product.

Preferably, the peroxycarboxylic acid is peracetic acid.

Preferably, the peroxycarboxylic acid is in the form of an aqueous solution with a concentration of 10% to 25%.

Preferably, the peroxycarboxylic acid is used in an amount of 50-1000 ppm based on the weight of pure monochloroacetic acid, preferably 100-500 ppm, most preferably 100-300 ppm.

Preferably, the peroxycarboxylic acid is used in an amount of 50-1000 ppm based on the weight of the dilute monochloroacetic acid, preferably 50-500 ppm, most preferably 50-100 ppm.

Preferably, the peroxidation process is carried out at a temperature of 20° C. to 100° C., in the case of neat monochloroacetic acid preferably at a temperature of 70-100° C., in the case of water-diluted monochloroacetic acid it is preferably 20-80° C.

In a preferred industrial scale embodiment, peroxycarboxylic acid in the form of an aqueous solution is added to the distilled monochloroacetic acid stream from the distillation unit in a suitable weight ratio to the weight of the monochloroacetic acid.

The probable cause of coloration of crude MCAA is trace contaminants of an organic nature, difficult to identify by analytical methods, sensitive to high temperature and formed, in particular in the initial period after replacement and/or when the fresh catalyst of the hydrogenation process is put into use, when the fresh hydrogenation catalyst shows very high activity and relatively low selectivity.

In the method according to the invention, the trace organic impurities are peroxidated with the peroxycarboxylic acid. Surprisingly, the expedient peroxidation of the crude MCAA according to the invention ultimately completely eliminates the undesirable colored oxidation intermediates from the finished product.

The use of such a solution allows to eliminate the phenomenon of aging of the product, which is manifested by a gradual change of color in the case of the liquid form from colorless to light yellow or light brown or light gray, and in the case of the solid form from white to light yellow or light brown or light pink.

As it is the last step in the production of monochloroacetic acid, it is possible to use aqueous solutions of peroxycarboxylic acids. Thanks to this, all risks related to their introduction at earlier stages of production have been eliminated.

Laboratory studies of the thermal stability of monochloroacetic acid products show that to obtain colorless, time-stable MCAA products, it is enough to add to the undiluted form of monochloroacetic acid obtained from the distillation process and stored in the operational tank in the case of: the undiluted form of MCAA in the amount of 50 to 1000 ppm, and in the case of the diluted form of MCAA from 50 to 1000 ppm of peroxycarboxylic acid to achieve complete thermal stability of the final product.

In the event that more peroxycarboxylic acid than necessary was added to the system, the system would remain stable and the final product would not be adversely affected, since the peroxycarboxylic acid is inert towards both monochloroacetic acid and dichloroacetic acid without changing their concentrations in the end products over time, which allows to always receive the product within the desired specification range.

The following examples illustrate the present invention.

EXAMPLES

The thermal stabilization test of monochloroacetic acid is performed on the test stand shown in FIG. 1, consisting of the following elements:
1. A jacketed mixing tank with a volume of 1 dm$^3$ equipped with a mechanical stirrer, temperature control in the range of 10° C.-100° C., nitrogen blanket.
2. Monochloroacetic acid dispenser
3. Peracetic acid dispenser
4. Circulation pumps with a work efficiency in the range of 0.1 dm$^3$/h-5 dm$^3$/h,
5. Sampling point
6. Needle valve for check-regulating the nitrogen blanket
7. Needle valve regulating the nitrogen blanket
8. Digital pressure gauge to control the nitrogen blanket
9. Granulation belt
10. Operational tank 1
11. Operational tank 2
12. Demineralized water dispenser
13. Static mixer
14. Operational tank 3

Before filling the mixing tank (1), the jacket heating is activated to heat the tank walls, and the nitrogen blanket is activated, which is controlled by two needle valves (6 and 7) and a digital pressure gauge (8). After the walls of the mixing tank (1) have heated up, monochloroacetic acid at a temperature of 70-100° C. is introduced into the reactor through the dispenser (2). After the mixing tank (1) is full, the mechanical stirrer is started. Then, an aqueous peroxycarboxylic acid solution is introduced through the dispenser (3). Then, after obtaining a homogeneous mixture, the circulation pump (4) is turned on to be able to control the color change of monochloroacetic acid under the influence of peroxycarboxylic acid by taking a sample through the sampling point (5). When monochloroacetic acid acquires the appropriate color, it is sent through the pump (4) to one of three nodes:
1. If the final product is to be a solid monochloroacetic acid in the form of flakes, monochloroacetic acid is dosed through the pump (4) to the granulating belt (9), where the production of monochloroacetic acid takes place and the product in the form of a flakes is stored in the operational tank (10) at ambient temperature.
2. If the end product is to be a liquid monochlorocotic acid, undiluted monochloroacetic acid is sent through the pump (4) to the operational tank (11), where the temperature is maintained at 70° C.
3. If the final product is to be a liquid monochlorocotic acid diluted with water, the monochloroacetic acid is sent through the pump (4) to the static mixer (13), where it is diluted to the appropriate concentration by demineralized water dosed by the dispenser (12). The finished product is stored in the operational tank (14), where the temperature is maintained at 25-40° C.

Example 1—Monochloroacetic Acid in Undiluted Liquid Form

The study of thermal stability of undiluted monochloroacetic acid begins with heating the mixing tank to a temperature of 70° C. in order to prevent the process of monochloroacetic acid crystallization on its walls, and creating a nitrogen blanket with a pressure of 0.01 bar (g). 1000 g of monochloroacetic acid at a temperature of 70° C., for which a color of 12 units on Hazen scale was measured, was placed in the mixing tank. Then, the mechanical stirrer is started and the acid temperature is maintained at 70° C., then 3.33 g of a 15% aqueous solution of peracetic acid is dosed into the mixing tank. Then, after obtaining the homogeneous mixture, the circulation pump is started and acid samples are taken through the sampling point at regular intervals. After obtaining a stable color of 36 units on Hazen scale, the monochloroacetic acid is sent by a pump to the operational tank, where it is then kept at 70° C. for a period of 7 days. After this period, the color of the product is determined again.

Parallel to the above test, a similar test is carried out on the same test stand, with the difference that no peracetic acid is added to the control sample of monochloroacetic acid.

The color measurement results are summarized in Table 2.

TABLE 2

Color change of undiluted liquid MCAA when stored at elevated
temperature (70° C.) for 7 days. The color level
was determined on Hazen scale. The color of the product
was measured at the beginning of the test (measurement
0) and after the selected test days (i.e., days 1 and 7).

| | Color in Hazen units - incubation at 70° C., day of measurement | | |
|---|---|---|---|
| Product: molten MCAA | 0 | 1 | 7 |
| CONTROL SAMPLE 100% MCAA (0) - peracetic acid free | <60 | >60 | >60 |
| TEST SAMPLE 100% MCAA (1) - with peracetic acid eq = 500 ppm | <60 | <60 | <60 |

Example 2—Solid Monochloroacetic Acid

The study of thermal stability of undiluted monochloroacetic acid begins with heating the mixing tank to the temperature of 70° C. in order to prevent the process of monochloroacetic acid crystallization on its walls, and creating a nitrogen blanket with a pressure of 0.01 bar (g). 1000 g of monochloroacetic acid at a temperature of 70° C., for which the color of 44 units on Hazen scale was measured, was placed in the mixing tank. Then, the mechanical stirrer is started and the acid temperature is maintained at 70° C., then 2.00 g of a 15% aqueous solution of peracetic acid is dosed into the mixing tank. Then, after obtaining the homogeneous mixture, the circulation pump is started and acid samples are taken through the sampling point at regular intervals. After obtaining a stable color at the level of 54 units on Hazen scale, monochloroacetic acid is sent by a pump to the granulating belt, where the monochloroacetic acid is packaged and the solid acid is produced in the form of flakes, which are then stored in a foil bag in the operational tank at ambient temperature. Monochloroacetic acid flakes are stored in a foil bag for 4 weeks at ambient temperature. After this period, the chloroacetic acid flakes are dissolved in water so as to obtain a liquid aqueous solution with 80% MCAA content, and the color of the resulting solution was then measured, which was 19 units on Hazen scale.

Parallel to the above test of test samples with the use of the same test apparatus, an analogous test is carried out with the difference that no peracetic acid is added to the control sample of monochloroacetic acid.

The color measurement results are summarized in Table 3.

TABLE 3

Color change of liquid 80% MCAA solution during incubation
at elevated temperature (40° C.) for 7 days, prepared
from flakes after storage at room temperature for 28
days. The color level was determined on Hazen scale.

| | | Color in Hazen units - incubation at 40° C., day of measurement | | |
|---|---|---|---|---|
| Product: MCAA flakes | Shelf life MCAA flakes in solid form | 0 | 1 | 7 |
| CONTROL SAMPLE MCAA flakes diluted to 80% MCAA - without peracetic acid | 28 days at ambient temperature | >20 | >20 | >20 |
| TEST SAMPLE MCAA flakes diluted to 80% MCAA - with peracetic acid eq = 300 ppm | 28 days at ambient temperature | <20 | <20 | <20 |

Example 3—Monochloroacetic Acid in Liquid
Form, Diluted with Water

The study of thermal stability of monochloroacetic acid in a liquid, diluted form begins with heating the mixing tank to the temperature of 70° C. in order to prevent the process of monochloroacetic acid crystallization on its walls, and creating a nitrogen blanket with a pressure of 0.01 bar (g). 800 g of monochloroacetic acid at a temperature of 70° C., for which the color of 39 units on Hazen scale was measured, was placed in the mixing tank. Then, the mechanical stirrer is started and the acid temperature is maintained at 70° C., and then 0.533 g of a 15% aqueous peracetic acid solution is dosed into the mixing tank. Then, after obtaining the homogeneous mixture, the circulation pump is started and acid samples are taken through the sampling point at regular intervals. After obtaining a stable color of 44 units on Hazen scale, the monochloroacetic acid is pumped to a static mixer where it is mixed with 200 g of demineralized water dispensed by a dispenser. The chloroacetic acid diluted in this way is sent to the operational tank for which the color of 15 units on Hazen scale was measured. Then it is kept at 40° C. for 7 days. After this period, the color of the product is determined again.

Parallel to the above test, a similar test is carried out on the same test stand, with the difference that no peracetic acid is added to the control sample of monochloroacetic acid.

The results of the color measurements are summarized in Table 4.

TABLE 4

Color change of 80% MCAA during storage at elevated temperature
(40° C.) for 7 days. The color level was determined
on Hazen scale. The color of the product was measured
at the beginning of the test (measurement 0) and after
the selected test days (i.e., days 1 and 7).

| Product: 80% MCAA | Color in Hazen units - incubation at 40° C., day of measurement | | |
|---|---|---|---|
| | 0 | 1 | 7 |
| 80% MCAA (1) - without peracetic acid | <20 | >20 | >20 |
| 80% MCAA (2) - with peracetic acid eq = 100 ppm | <20 | <20 | <20 |

The invention claimed is:

1. A method for producing a colorless monochloroacetic acid, comprising a crude monochloroacetic acid peroxidation step, wherein the peroxycarboxylic acid, is added to the crude monochloroacetic acid in liquid form in an amount of at least 50 ppm based on the weight of the crude monochloroacetic acid for a peroxidation reaction and the peroxidation reaction is carried out at a temperature of 20° C. to 100° C. until a colorless product with a color level below 100 units on Hazen scale is obtained, then, if necessary, cooled to room temperature, optionally added with water and packed, wherein a pure monochloroacetic acid in molten form or a water-diluted monochloroacetic acid with a concentration above 60 wt %, is used as crude monochloroacetic acid.

2. The method according to claim 1, wherein the peroxycarboxylic acid is peracetic acid.

3. The method according to claim 1, wherein the peroxycarboxylic acid is used in the form of an aqueous solution with a concentration of 10% to 25% of the peroxycarboxylic acid.

4. The method according to claim 1, wherein the peroxycarboxylic acid is used in an amount of 50-1000 ppm based on the weight of the pure monochloroacetic acid.

5. The method according to claim 1, characterized in that the peroxycarboxylic acid is used in an amount of 50-1000 ppm based on the weight of the diluted monochloroacetic acid.

6. A colorless monochloroacetic acid, wherein it maintains a coloration of less than 60 units on Hazen scale for at least 7 days when stored at a temperature of not more than 70° C.

7. The monochloroacetic acid according to claim 6, wherein it has a form selected from:
100% monochloroacetic acid in solid form,
100% monochloroacetic acid in molten form, or
water-diluted monochloroacetic acid with a concentration of 60 wt % to 90 wt % in liquid form.

8. The monochloroacetic acid according to claim 6, wherein it has been obtained by a method according to claim 1.

9. The method according to claim 1, wherein water-diluted monochloroacetic acid with a concentration from 60% wt % to 90 wt % is used as crude monochloroacetic acid.

10. The method according to claim 4, wherein the peroxycarboxylic acid is used in an amount of 100-500 ppm based on the weight of the pure monochloroacetic acid.

11. The method according to claim 4, wherein the peroxycarboxylic acid is used in an amount of 100-300 ppm based on the weight of the pure monochloroacetic acid.

12. The method according to claim 5, wherein the peroxycarboxylic acid is used in an amount of 50-500 ppm based on the weight of the diluted monochloroacetic acid.

13. The method according to claim 5, wherein the peroxycarboxylic acid is used in an amount of 50-100 ppm based on the weight of the diluted monochloroacetic acid.

14. The method according to claim 1, wherein the peroxidation reaction is carried out at a temperature of 70-100° C. for undiluted monochloroacetic acid.

15. The method according to claim 1, wherein the peroxidation reaction is carried out at a temperature of 20-80° C. in the case of water-diluted monochloroacetic acid.

16. The monochloroacetic acid according to claim 7, wherein it has a form of flakes of 100% monochloroacetic acid.

* * * * *